(12) United States Patent
Richard et al.

(10) Patent No.: US 6,929,648 B2
(45) Date of Patent: Aug. 16, 2005

(54) PROSTHETIC VASCULAR GRAFT CONNECTOR

(75) Inventors: Thierry Richard, Florham Park, NJ (US); John K. Edoga, Morristown, NJ (US)

(73) Assignee: Edrich Vascular Devices, Inc., Morristown, NJ (US)

( * ) Notice: Subject to any disclaimer, the term of this patent is extended or adjusted under 35 U.S.C. 154(b) by 0 days.

(21) Appl. No.: 10/888,276

(22) Filed: Jul. 9, 2004

(65) Prior Publication Data

US 2004/0254595 A1 Dec. 16, 2004

Related U.S. Application Data

(62) Division of application No. 10/405,805, filed on Apr. 2, 2003, now Pat. No. 6,896,688.
(60) Provisional application No. 60/410,205, filed on Sep. 12, 2002.

(51) Int. Cl.$^7$ ................................................ A61B 17/08
(52) U.S. Cl. ...................................... 606/153; 606/151
(58) Field of Search ............................... 606/151–157, 606/139; 623/1.13, 1.36, 3.26, 1.23; 285/241–244, 239, 257, 319, 921

(56) References Cited

U.S. PATENT DOCUMENTS

| | | | |
|---|---|---|---|
| 3,357,432 A | 12/1967 | Sparks | 128/334 |
| 3,435,823 A | 4/1969 | Edwards | 128/334 |
| 3,683,926 A | 8/1972 | Suzuki | 128/334 R |
| 4,214,586 A | 7/1980 | Mericle | 128/334 |
| 4,267,842 A | 5/1981 | Archibald | 128/334 R |
| 5,776,185 A | 7/1998 | Verona et al. | 623/1 |
| 5,868,763 A | 2/1999 | Spence et al. | 606/153 |
| 6,007,576 A | 12/1999 | McClellan | 623/1 |
| 6,030,392 A | 2/2000 | Dakov | 606/139 |
| 6,152,937 A | 11/2000 | Peterson et al. | 606/153 |
| 6,231,085 B1 | 5/2001 | Olson | 285/23 |
| 6,235,054 B1 | 5/2001 | Berg et al. | 623/1.36 |
| 6,350,280 B1 | 2/2002 | Nash et al. | 623/1.36 |
| 6,371,981 B1 | 4/2002 | Yang et al. | 623/1.13 |
| 6,402,767 B1 | 6/2002 | Nash et al. | 606/153 |
| 6,419,681 B1 | 7/2002 | Vargas et al. | 606/153 |
| 6,428,550 B1 | 8/2002 | Vargas et al. | 606/153 |
| 6,461,320 B1 | 10/2002 | Yencho et al. | 604/8 |
| 6,464,709 B1 | 10/2002 | Shennib et al. | 606/155 |
| 6,641,177 B1 | 11/2003 | Pinciaro | 285/242 |
| 2002/0087175 A1 | 7/2002 | Gifford, III et al. | 606/153 |

FOREIGN PATENT DOCUMENTS

| | | |
|---|---|---|
| FR | 2683141 | 5/1993 |
| WO | WO 87/04915 | 8/1987 |
| WO | WO 88/06865 | 9/1988 |

*Primary Examiner*—Tan-Uyen T. Ho
(74) *Attorney, Agent, or Firm*—Wiggin and Dana LLP; Gregory H. Rosenberg; Anthony P. Giangi

(57) ABSTRACT

Two prostheses each have a tubular sidewall with a terminal portion extending to a connection end. A connector body has first and second terminal portions extending to first and second ends. The connector body terminal portions are respectively surrounded by the prostheses terminal portions. First and second straps respectively circumscribe the prostheses terminal portions to bias the prostheses into engagement with the connector body. The connector body has first and second strap engagement projections respectively captured by apertures in the straps.

13 Claims, 14 Drawing Sheets

PROSTHETIC VASCULAR GRAFT CONNECTOR

CROSS REFERENCE TO RELATED PATENT APPLICATION

This patent application is a divisional of U.S. patent application Ser. No. 10/405,805, entitled "Prosthetic Vascular Graft Connector," filed on Apr. 2, 2003, now U.S. Pat. No. 6,896,688, which relates to and claims priority to U.S. provisional patent application No. 60/410,205, entitled "Prosthetic Vascular Graft Connector," that was filed on Sep. 12, 2002. The subject matter of that provisional patent application is incorporated by reference in its entirety herein.

BACKGROUND OF THE INVENTION (1) Field of the Invention

This invention relates to a connector for interconnecting a first prosthetic vessel to a second prosthetic vessel, such as during reconstructive surgery. More particularly, the connector facilitates the rapid durable joining of a prosthetic graft to a bodily vessel or organ thereby reducing cross-clamp time to enhance recovery.

(2) Description of the Related Art

Vascular reconstructive surgery is utilized to replace portions of blood vessels damaged by aneurismal and occlusive diseases. One such type of replacement is an end-to-end anastomosis where a blood vessel is cut on either side of a diseased or damaged portion. Prosthetic devices are joined to the cut ends of the healthy portions of the blood vessel and a connector joins the prosthetic devices completing a vessel for the flow of blood that by-passes the damaged portion. Among the objectives of vascular reconstructive surgery is to minimize exsanguination at interfaces between the blood vessels and the prostheses and at interfaces between the prostheses, to minimize cross-clamp time (the time that the blood vessel is externally deprived of blood flow) and to minimize thrombogenicity (the formation of blood clots). The rate of the formation of blood clots tends to increase when flowing blood contacts different materials and when turbulence is introduced into the blood flow.

Exsanguination is minimized by a tight seal between the vessel and the prosthesis and between interconnected prostheses. Sutures and surgical staples are effective to achieve a tight seal between a prosthesis and a blood vessel and are widely used in vascular reconstructive surgery. Sutures and surgical staples are less efficient to form a tight seal between two prostheses.

As a replacement to sutures and surgical staples, it is known to interconnect a prosthesis to a blood vessel with an external clamp. Such clamps are disclosed in U.S. Pat. Nos. 3,357,432; 3,435,823 and 6,402,767, all three of which are incorporated by reference herein in their entireties. Generally, the prosthesis is inserted into the end of the vessel. The prosthesis has a locking structure on an external surface, such as detents or barbs. An external clamp or ring then closes about the vessel portion overlying the locking structure to thereby hold the vessel firmly in place. Due to the small scale of the vessels, manipulation and accurate placement of the locking structure has, to date, proven difficult.

Another vascular prosthesis connector is disclosed in FR2683141 by Thierry Richard and Eric Perouse entitled "Connection device for organ vessel prostheses."

Accordingly, there remains a need for an effective mechanism to rapidly seal a first vascular prosthesis to a second vascular prosthesis that does not have the disadvantages recited above.

BRIEF SUMMARY OF THE INVENTION

In one aspect, the invention is directed to a vascular prosthesis and connector assembly. Two prostheses each have a tubular sidewall with a terminal portion extending to a connection end. A connector body has first and second terminal portions extending to first and second ends. The connector body terminal portions are respectively surrounded by the prostheses terminal portions. First and second straps respectively circumscribe the prostheses terminal portions to bias the prostheses into engagement with the connector body. The connector body has first and second strap engagement projections respectively captured by apertures in the straps.

In one embodiment of this aspect, the vascular prosthetic surface is everted about a connector.

In another embodiment of this aspect, a connector is pre-attached to either one or both ends of vascular prostheses.

Other aspects relate to methods of use and kits containing the subject connectors.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
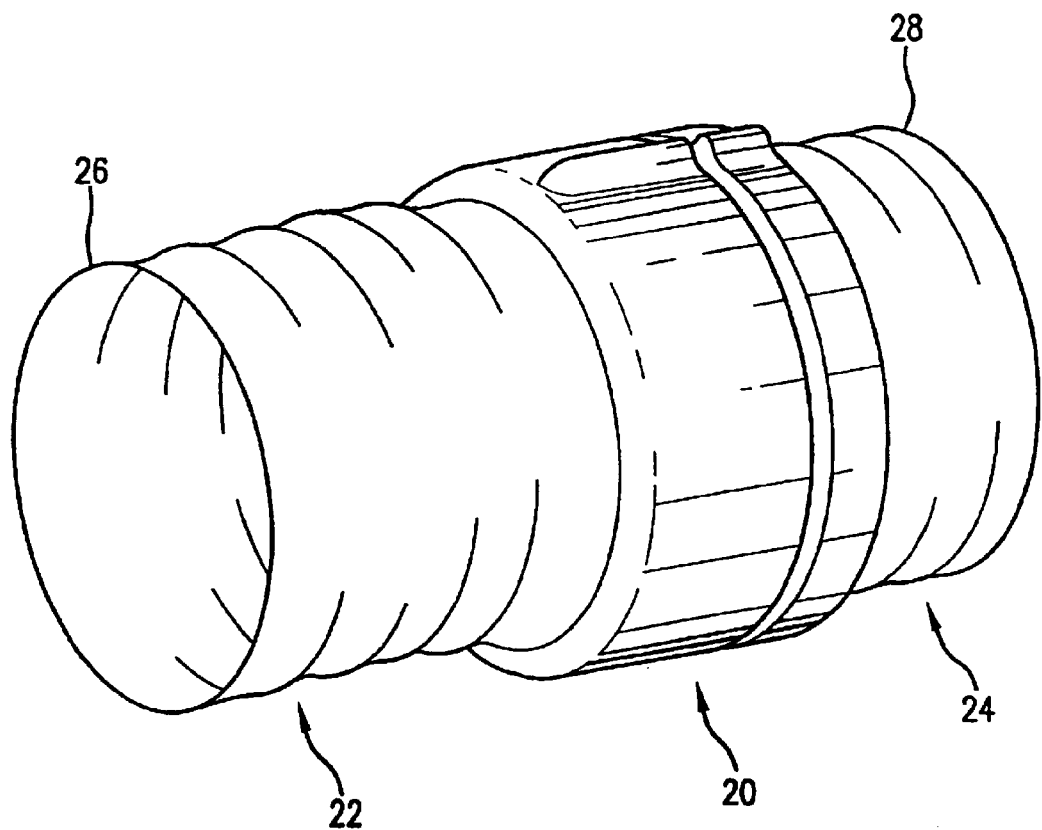
FIG. 1 is a view of a vascular prosthesis connector.

FIG. 1 shows a connector 20 for connecting a first end of a first vascular prosthesis 22 to a first end of a second vascular prosthesis 24 to by-pass a diseased or damaged portion of a blood vessel. Opposing second ends 26, 28 of the first 22 and second 24 vascular prostheses are joined to cut ends of healthy portions of the blood vessel on either side of the diseased or damaged portion. The opposing second ends may be joined to the blood vessels by conventional methods such as sutures or surgical staples. Further, use of the connector is not limited to human reconstructive surgery and may be used in veterinary applications as well.

Figure 2:
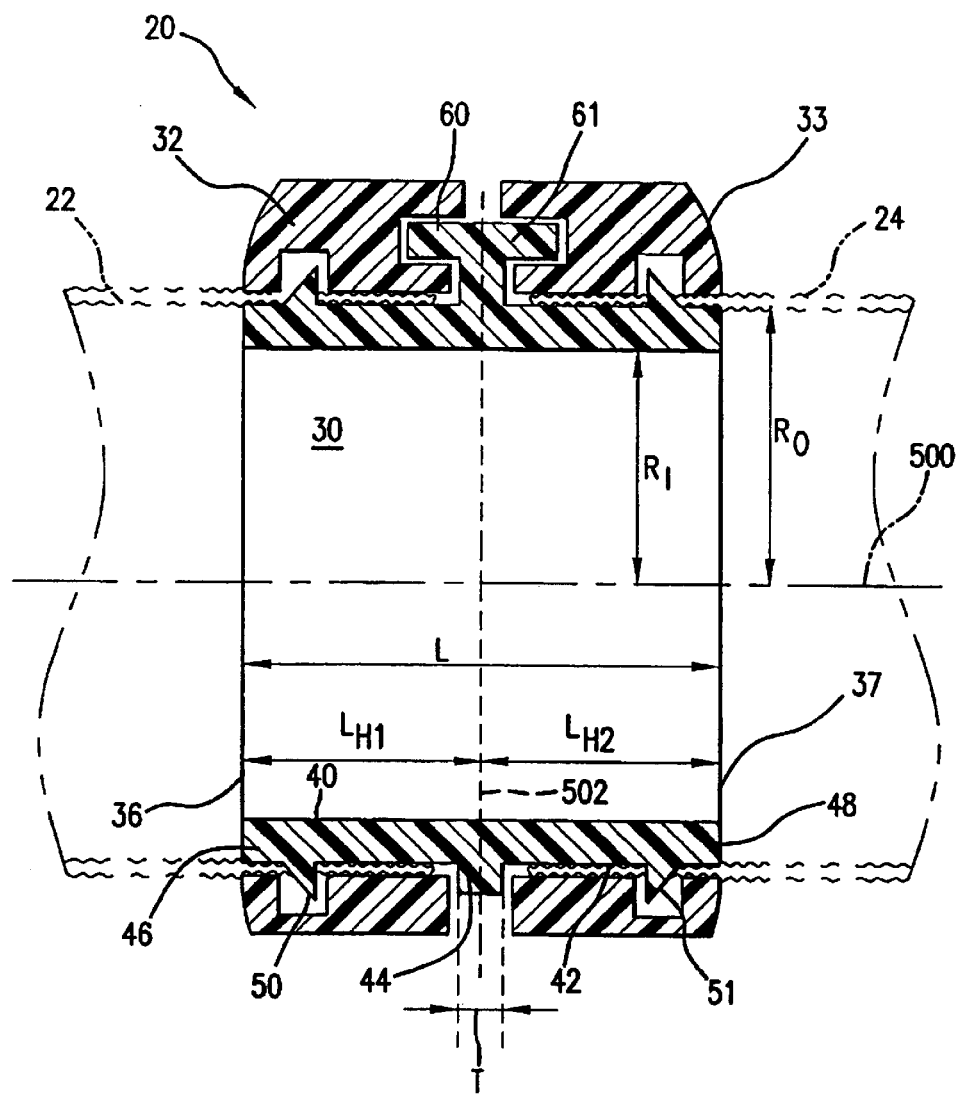
FIG. 2 is a longitudinal sectional view of the connector of FIG. 1.

An exemplary connector 20 is shown in cross-sectional representation in FIG. 2 and includes a connector body 30, a first strap 32 and a second strap 33. The connector body 30 is manufactured from any biocompatible material, including metals, plastics and carbon compounds, for example polyethylene or a pyrolytic carbon compound. Preferably, the connector body 30 is formed as a unitary molding from an injection molded plastic. The connector body 30 has a generally tubular structure configuration and extends for a length L along a central longitudinal axis 500 between first rim 36 and second rim 37 that define respective first and second ends of the connector body. The length "L" is dependent on the application. For an exemplary aortic anastomosis, "L" is from about 12 millimeters to about 14 millimeters. The connector body 30 has an inner (interior) surface 40 with a principal radius $R_I$ and an outer (exterior) surface 42 with a principal radius $R_O$. For the exemplary aortic anastomosis, $R_I$ is from about 18 millimeters and $R_O$ is from about 20 millimeters to about 24 millimeters. Typically, $R_O$ is about 10% greater than $R_I$.

A flange 44 extends radially outward from the connector body 30 along a central transverse plane 502 that divides the body into two halves. The exemplary flange has an outer radius $R_F$ (FIG. 5) that is from about 1.5 millimeter a thickness T of from about 0.5 millimeter. As shown in FIG. 2, central transverse plane 502 bisects the flange 44 and separates first connector body portion 46 from second connector body portion 48 with each tube portion having a respective length, $L_{H1}$ or $L_{H2}$. $L_{H1}$ is typically, but not necessarily equal to $L_{H2}$.

Figure 4:
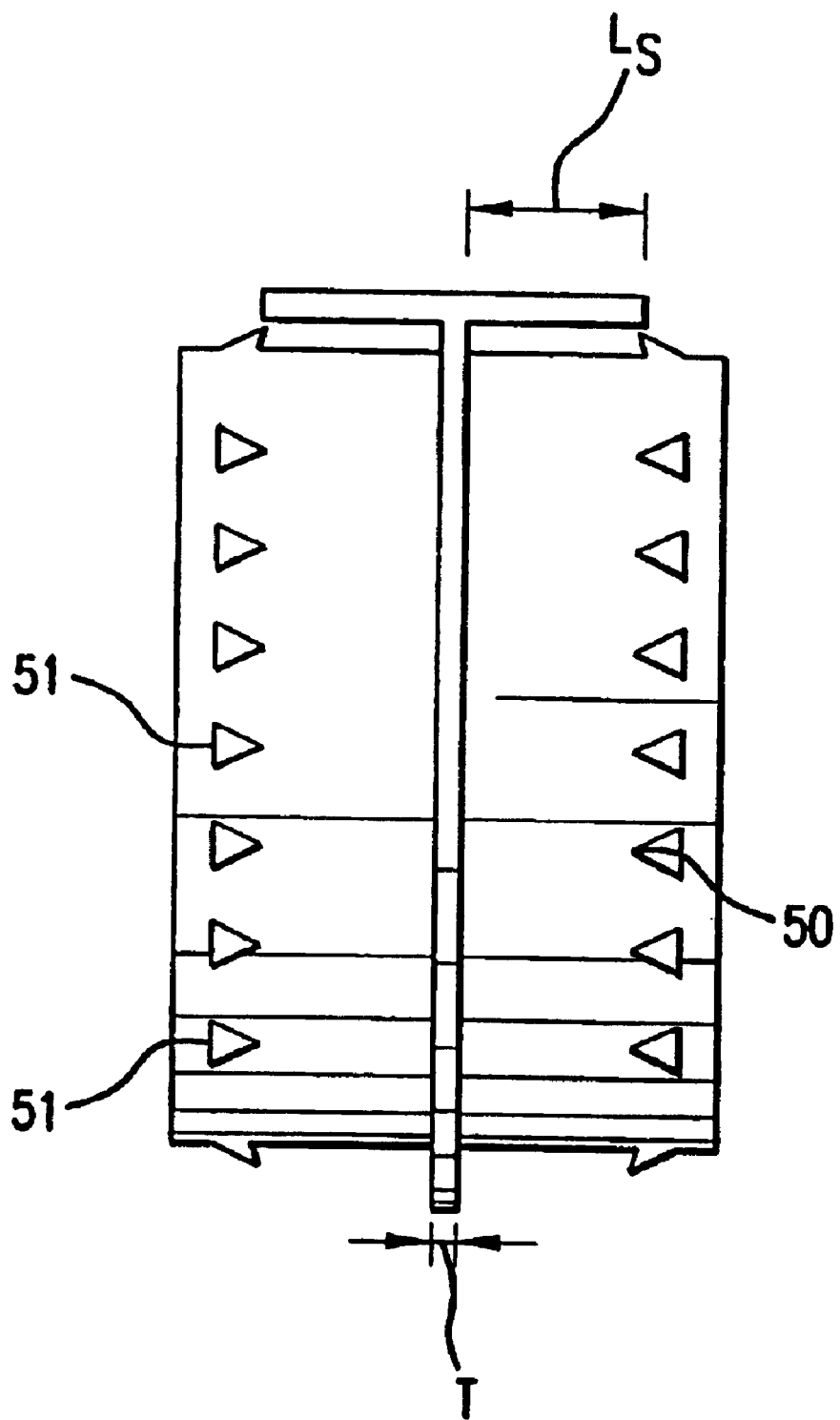
FIG. 4 is a side view of the body of FIG. 3.
Figure 5:
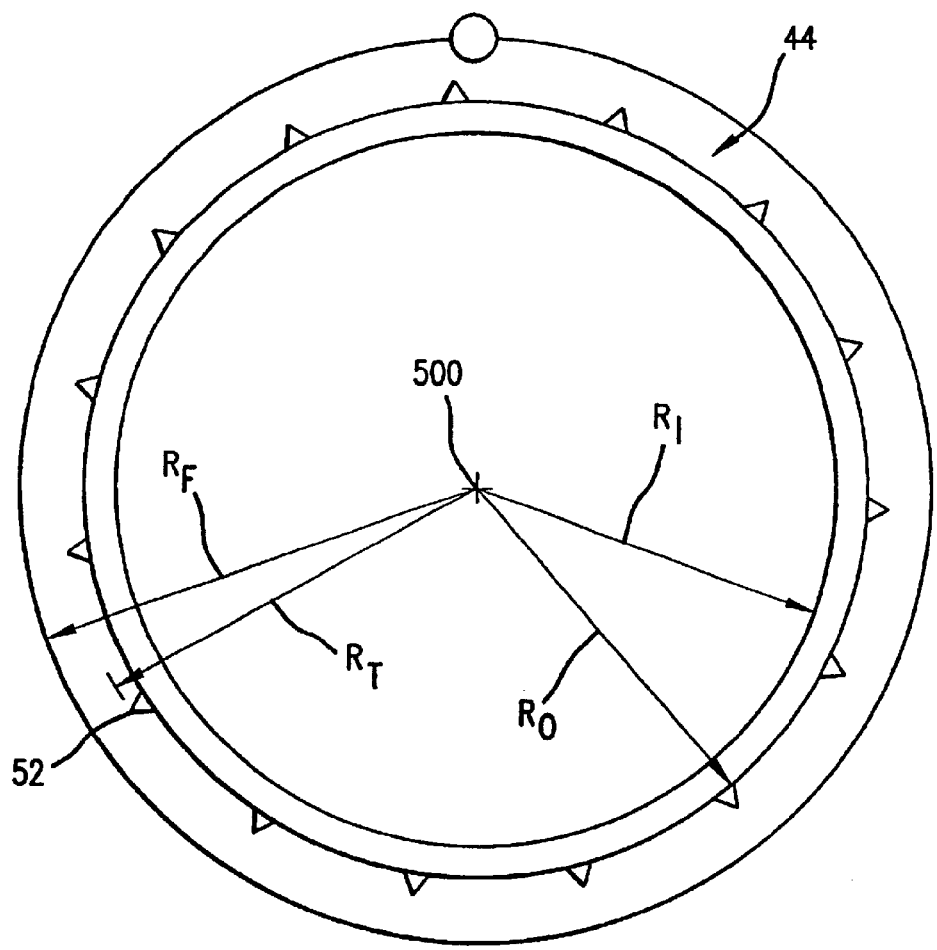
FIG. 5 is an end view of the body of FIG. 3.

Along a peripheral surface of the first 46 and second 48 connector body portions, offset from the associated rim 36 and 37, a first circumferential array of detents 50 and a second circumferential array of detents 51 extend radially exterior from the outer surface 42 to an apex 52 at a radius $R_T$ (see FIGS. 4 and 5). Described in further detail below, the detents 50, 51 extend upward from the exterior surface 42 (see FIG. 2) for a distance effective to engage and retain the prostheses 22, 24. Typically, the detents extend upward from the exterior surface 42 for a distance of about 1 millimeter when formed from plastic. Somewhat smaller detents are effective when formed from metal.

Figure 3:
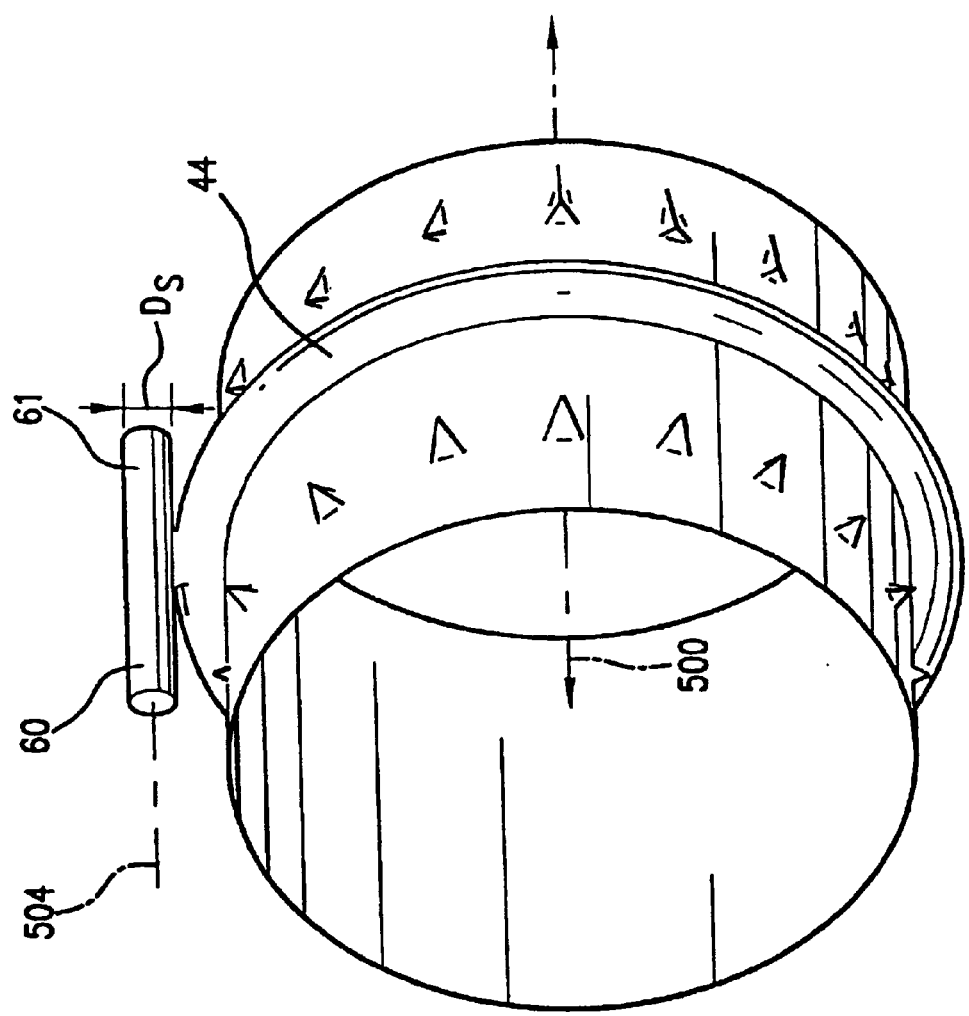
FIG. 3 is a view of a body of the connector of FIG. 1.

A pair of opposed shafts 60 and 61 shown in FIGS. 2 and 3 extend from the flange 44 along an axis 504 shown parallel to the axis 500. Exemplary shafts are of circular section of diameter $D_S$ and length $L_S$ (as shown in FIG. 4). Each shaft is spaced radially outboard from its associated portion 46, 48 of the connector body 30. Described in further detail below, the shafts 60, 61 may serve as a handle for maneuvering the connector body and may serve to position the associated straps 32 and 33. The shafts enable the prosthesis to be easily and accurately manipulated even during laparoscopic surgery and other procedures with limited access for the surgeon. The shafts may be formed to be removable from the connector body, integral with the connector body, or unitary with the connector body, such as when formed as part of the same molded piece.

Figure 6:
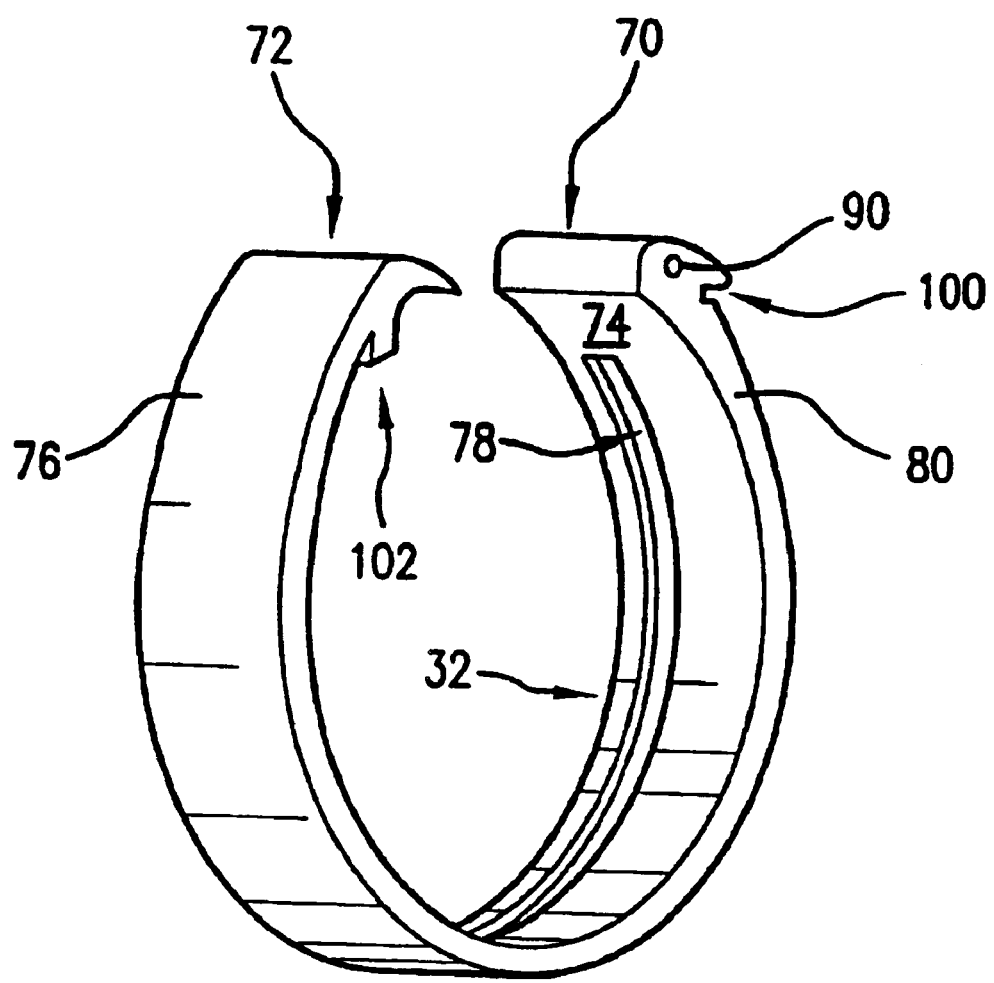
FIG. 6 is a view of a strap of the connector of FIG. 1.

FIG. 6 shows an exemplary strap 32. Depending on positioning circumstances, such a strap or a mirror image thereof could be utilized as either of the straps 32 and 33. The strap extends from a proximal end 70 to a distal end 72 and has generally inner (interior) and outer (exterior) surfaces 74 and 76. The strap inner surface has a channel 78 dimensioned to accommodate the associated detents, (e.g., 50 or 51 of FIG. 2) and portions of the associated prosthesis (e.g., 22 of FIG. 2) pushed into the channel by such detents. Advantageously, at an inboard side of the strap, there is a generally radial surface 80 joining the surfaces 76 and 78. At an outboard side of the strap, the strap largely tapers, with the outer surface 76 tapering inward to meet the inward surface 74. A blind longitudinal hole or compartment 90 extends from the surface 80 and for receiving the associated shaft 60, 61.

A channel 100 is provided in the outer surface 76 slightly recessed from the compartment 90. A complementary projection 102 is provided extending radially inward from the inner surface 74 near the distal end 72. In an engaged condition (described below), the channel 100 receives the projection 102 to lock the strap in a ring-like state. When locked, the strap prevents relative movement between the prostheses and the connector body. The locking of the strap is reversible. The strap may be disengaged by separating the projection from the channel. When the strap is unlocked, the connector may be further manipulated or replaced. Alternatively, other locking methods may be employed.

Figure 8:
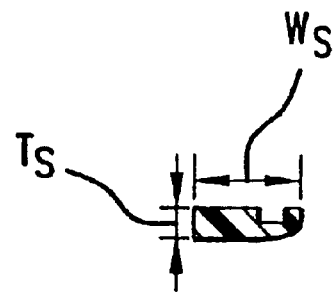
FIG. 8 is a cross sectional view of the strap of FIG. 7 taken along line 8—8.
Figure 9:
FIG. 9 is a sectional view of the strap of FIG. 7 taken along line 9—9.
Figure 7:
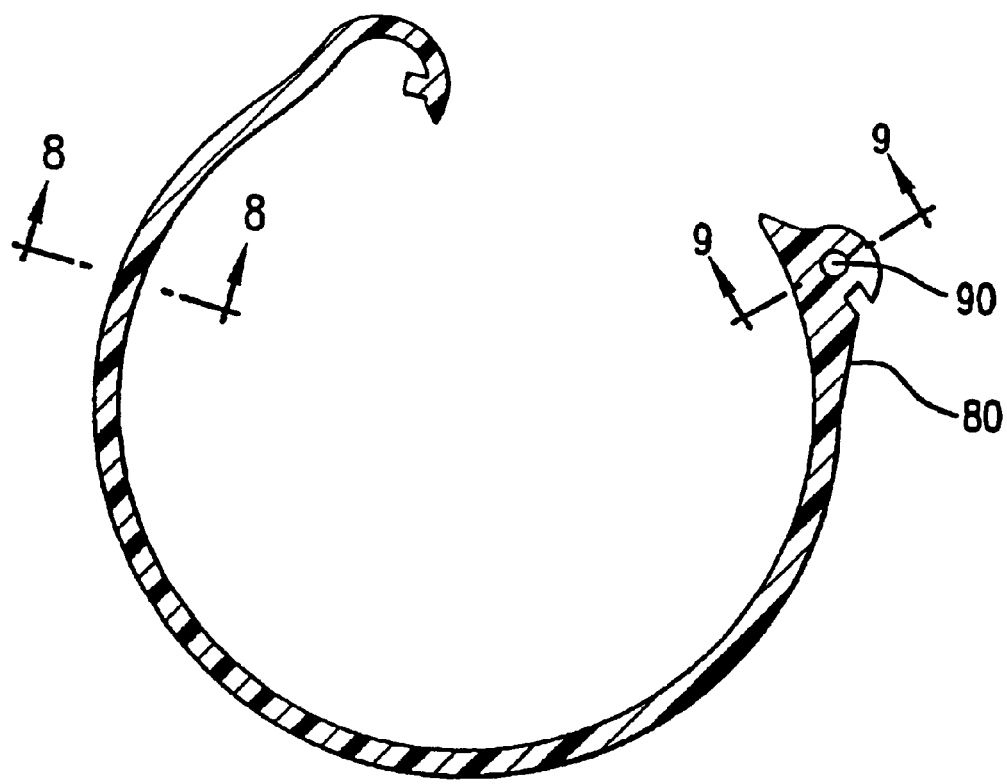
FIG. 7 is a connector end view of the strap of FIG. 6.

FIG. 7 is an end view of a strap while FIGS. 8 and 9 illustrated selected portions of the strap in cross-sectional representation.

Figure 10:
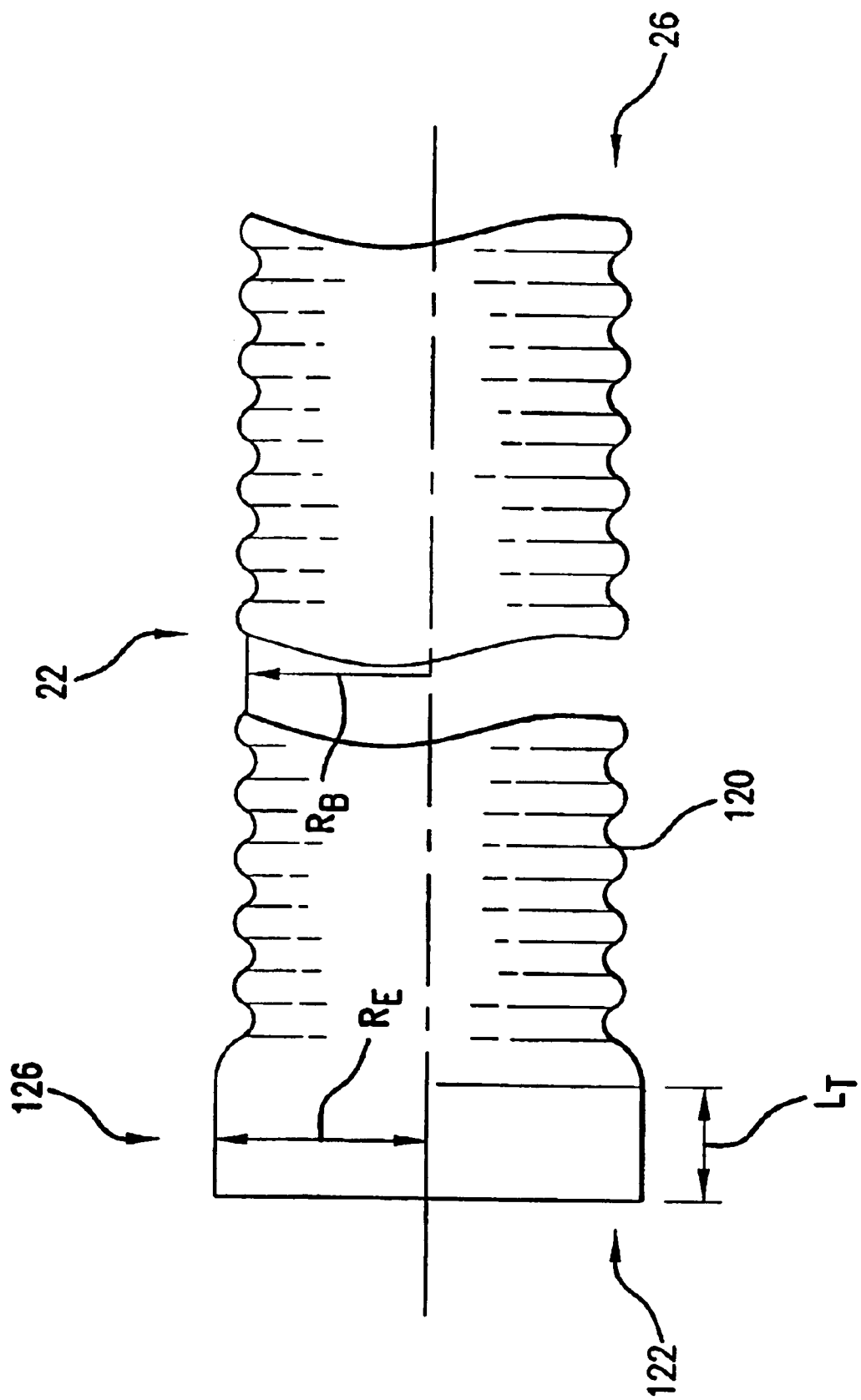
FIG. 10 is a longitudinal sectional view of a prosthesis.

FIG. 10 shows an exemplary vascular prosthesis 22 having a generally tubular body 120 extending from a first end 122 to an opposing second end 26. The exemplary body is formed of woven or knitted polyester or other suitable fabric. One preferred polyester is poly (ethylene terephthalate), such as Dacron (manufactured by DuPont of Wilmington, De.). A major portion of the tubular body 120 has an internal radius $R_B$. The illustrated embodiment includes an enlarged terminal portion 126 adjacent the first end 122. The exemplary terminal portion extends over length $L_T$ and, over a major portion thereof, has an internal radius $R_E$. The terminal portion is provided for coupling to the connector 20 with an associated portion of the connector body 30 being received within the enlarged terminal portion 126. The radius $R_E$ may be chosen relative to the radius $R_O$ to provide insertion of the connector with appropriate snugness. The radius $R_B$ may be chosen relative to the radius $R_I$ so that, when the prosthesis is installed and carrying blood, the connector does not provide an undue flow restriction (e.g., $R_I$ is chosen to be equal to $R_B$).

Figure 11:
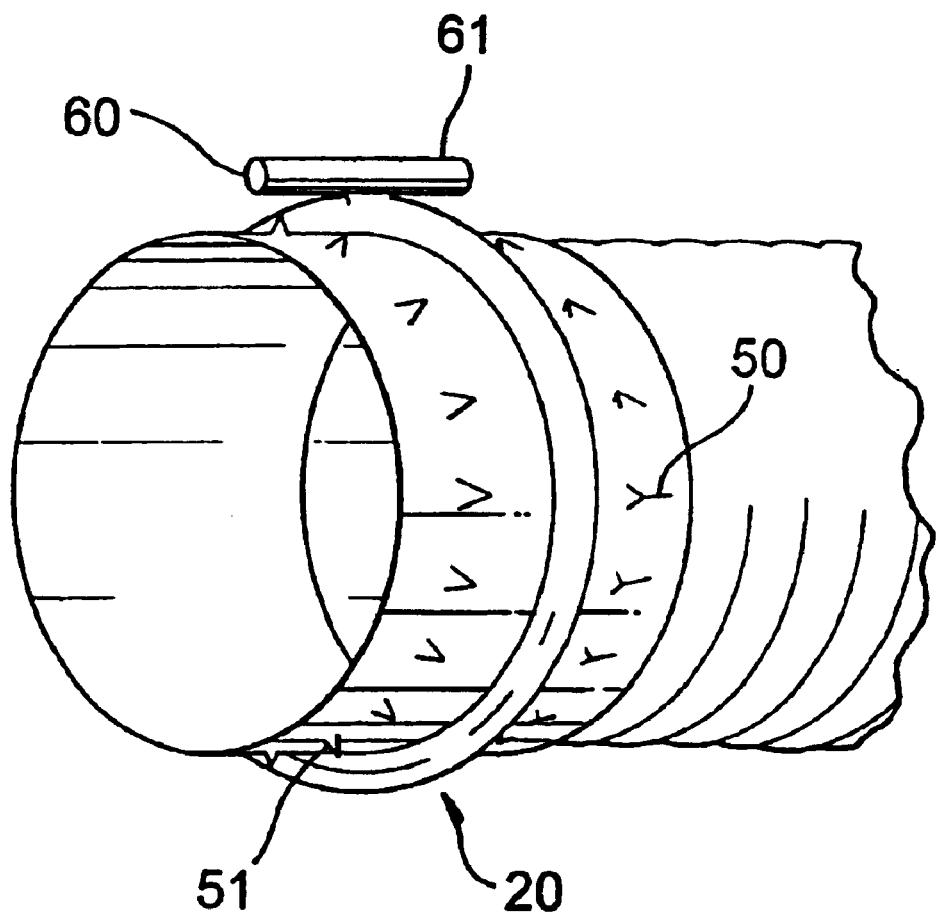
FIG. 11 is a view of the prosthesis installed on the connector body.
Figure 12:
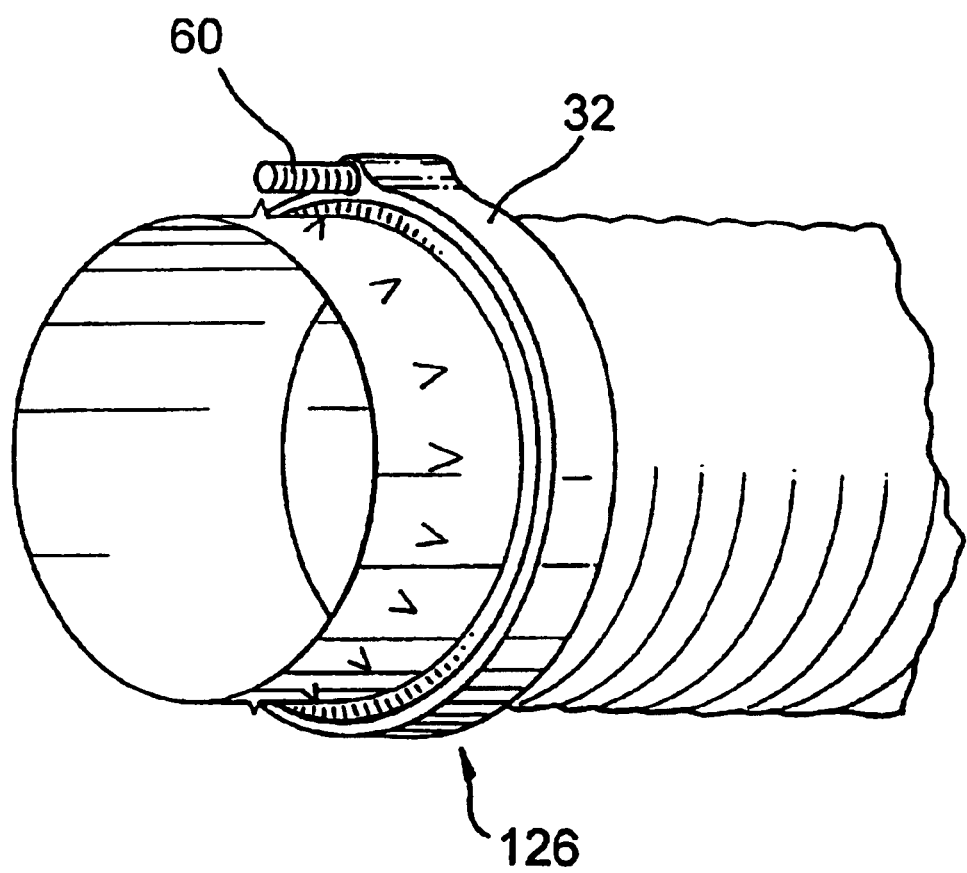
FIG. 12 is a view of the installed prosthesis of FIG. 11 circumscribed by a strap.

In one application of the connector of the invention, a vascular reconstructive surgical procedure entails coupling the second ends 26 of two prostheses to healthy portions of the patient's cardiovascular system on either side of a diseased or damaged portion and securing the connector to both first end 122 enlarged terminal portions 126 to couple the two prostheses. The connector may be pre-secured to one of the prostheses before the surgeon installs such prosthesis. The surgeon may so pre-secure (pre-install) or the packaged prosthesis may come with the connector pre-installed. To install each half of the connector to its associated prosthesis, the surgeon inserts a connector body portion (46, 48 in FIG. 2) into the enlarged terminal portion 126. This may be done by holding the connector body with a surgical instrument. For example, with reference to FIG. 11, the connector 20 may be held by one or both of the shafts 60, 61. The prosthesis enlarged terminal portion is then drawn over the tube portion 46 or 48, advantageously with a slight degree of stretch so as to firmly engage the detents 50. Advantageously the detents are pointed and point outward from the connector body to pierce the terminal portion and resist its retraction. With reference to FIG. 12, when the terminal portion is installed, the surgeon then installs the associated strap 32. This is done by manipulating the strap 32 with the associated shaft 60 and wrapping the strap around the terminal portion 126, finally inserting the projection 102 into the channel 100 (as illustrated in FIG. 6) to lock the strap 32 in its installed condition.

The connector body is advantageously formed of an appropriate plastic having sufficient rigidity to withstand the pressure envelope of the patient's viscera and is further biologically inert within the human body. Such plastics are dimensioned to a size effective to withstand arterial pressures of up to 300 millimeters. Preferred plastics include polyurethane and polyethylene. Other biocompatible materials such as metals and carbon compounds are also suitable. The connector may be dimensioned for particular applications. Size may be conveniently designated by an appropriate diameter or associated radius such as the interior diameter or its associated radius $R_I$. In an exemplary 20 mm embodiment, the radius $R_I$ is 10 mm and the radius $R_O$ is 11 mm. The 20 mm embodiment is near the large end of a size spectrum. Near the small end of that spectrum, an exemplary 6 mm embodiment has a radius $R_I$ of 3 mm and a radius $R_O$ of 4 mm. The scaling of connector body wall thickness relative to size will be largely influenced by structural integrity considerations. Accordingly, the wall thickness may increase less than proportionately.

The detent height is $R_T$–$R_O$ and is influenced principally by the material and thickness of the prostheses. Exemplary woven polyester prostheses have a wall thickness of 0.3–0.4 mm for such material, exemplary detent height is about twice the prosthesis wall thickness (e.g. about 1–3 times) or approximately 1 mm. The length $L_H$ will be influenced by structural integrity considerations and by considerations relating to the ease of assembling the prosthesis and strap to the body weighed against compactness considerations. An $L_H$ of about 2.5 mm may be a practical minimum. For the relatively small exemplary 6 mm size, an $L_H$ of about 3 mm may be appropriate. For the relatively large exemplary 20 mm size, an $L_H$ of about 5 mm may be appropriate. An exemplary flange thickness T is 1 mm. The detents advantageously fall along the outboard half of the length $L_H$. The handle shaft length $L_S$ is advantageously about half $L_H$ to avoid clearance problems relative to the detents.

An exemplary strap is molded of an appropriate plastic that is biologically inert within the body. Suitable plastics include polyethylene or polyurethane with a thickness of about 3 millimeters. An exemplary principal thickness $T_S$ is about 2 mm and an exemplary width $W_S$ is equal to $L_H$. Advantageous values of $T_S$ may be relatively insensitive to size. The flange radius $R_F$ is advantageously the same as the outer radius of the installed straps.

Figure 13:
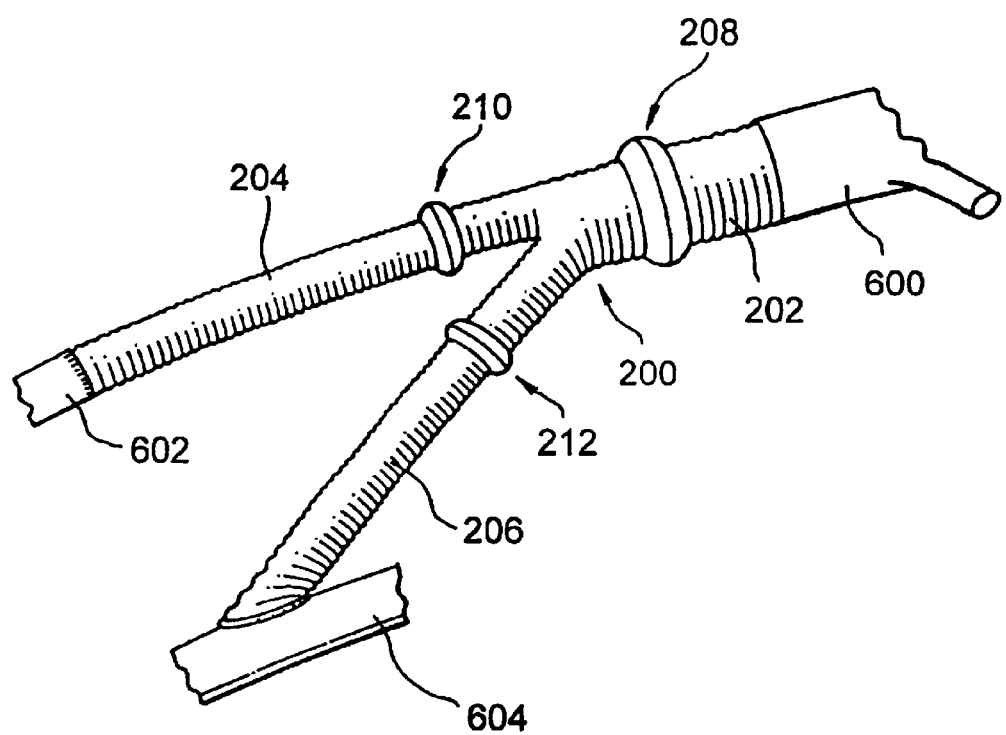
FIG. 13 is a view of a modular aorto-biiliac bypass.

FIG. 13 shows a flow-splitting prosthesis ("flow splitter") 200 installed in an aorto-biiliac bypass establishing communications between a patient's aorta 600 and iliac arteries 602 and 604. The flow splitter 200 is generally Y-shaped, having a leg or trunk 202 and a pair of first and second arms or branches 204 and 206. The flow splitter 200 is coupled to the arteries by respective connection prostheses 202, 204, and 206. The flow splitter 200 is coupled to the prostheses 202, 204, and 206 via respective couplers 208, 210, and 212. Except as otherwise described, these couplers may be otherwise similar to the connector (illustrated in either FIG. 2 or FIG. 15 as described below) and have similar interaction with the associated prostheses.

Prior to surgery, the sizes of the prostheses 202, 204, and 206 will be selected based upon medical imaging. Most key is the cross-sectional area characterized by a diameter or radius. Length may also be relevant and may be used to either select a particular prosthesis or cut a prosthesis to a particular length. By way of example, the prostheses 202, 204, and 206 may have nominal diameters of eighteen, eight and ten mm, respectively in one common size combination.

Figure 14:
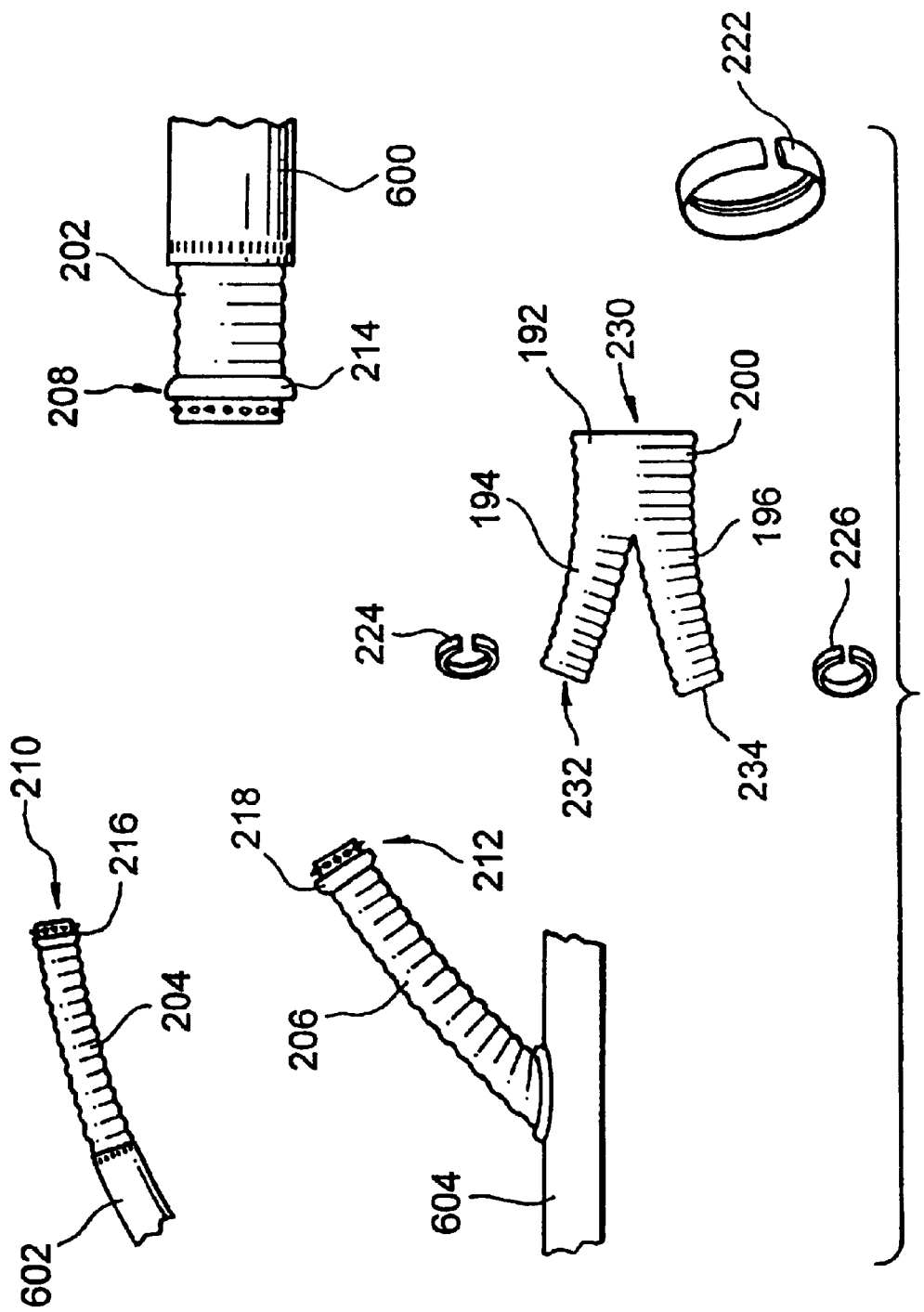
FIG. 14 is an exploded view of the bypass of FIG. 13.

With reference to FIG. 14, in an exemplary surgical procedure, the bodies of the couplers 208, 210, and 212 are preinstalled on associated ends of the prostheses 202, 204, and 206. They may be so installed with respective straps 214, 216, and 218. Alternatively, they may be secured by other means for example when only the other half of each connector body is adapted for receipt of such straps.

The components illustrated in FIG. 14 may be provided in kit form. For example. Prostheses 202, 204 and 206 are supplied from a medical supply house with connectors 208, 210 and 212 pre-attached. The kit would further include a required prostheses 200 and a number of locking straps 222, 224 and 226. It is preferred, but not required, that the connectors 208, 210 and 212 would be of similar configuration such that locking straps 222, 224 and 226 are interchangeable.

The surgeon secures the connection prostheses 202, 204, and 206 to their associated arteries. In the illustrated example, the connection prosthesis 202 is surgically stapled to the aorta 600 in an end-to-end anastomosis. Suturing is an alternative. The connection prosthesis 204 is also secured to its iliac artery 602 via an end-to-end anastomosis such as via stapling or suturing. The connection prosthesis 206 is connected to its iliac artery 604 via an end-to-side anastomosis such as via suturing or stapling.

After installation of the connection prostheses 202, 204, and 206, the surgeon may install flow splitter 200. If the coupler bodies are preinstalled at the factory to their associated connection prostheses 202, 204, and 206, rings 222, 224, and 226 may be prepackaged with such connection prostheses. Alternatively, such rings may be prepackaged with the flow splitter 200 or otherwise provided. With the connection prostheses 202, 204, and 206 installed, the surgeon may finally size the flow splitter 200 by removing distal lengths of one or more of the trunk 192, first branch 194, and second branch 196 to define final ends 230, 232, and 234, respectively. Terminal portions adjacent to these ends are in turn placed by the surgeon over associated end portions of the bodies of connectors 208, 210, and 212 and secured with straps 222, 224, and 226. Blood flow is then reestablished and the surgery site closed.

Figure 15:
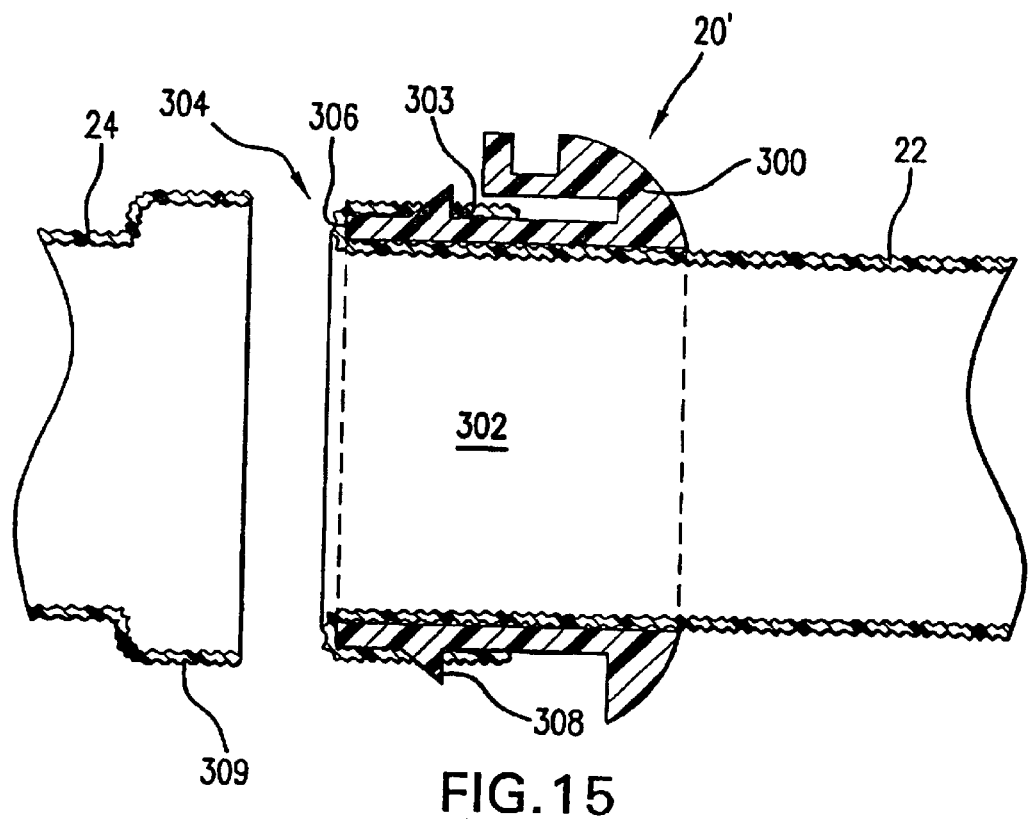
FIG. 15 is a cross-sectional representation of a connector body in accordance with a second embodiment of the invention.
Figure 16:
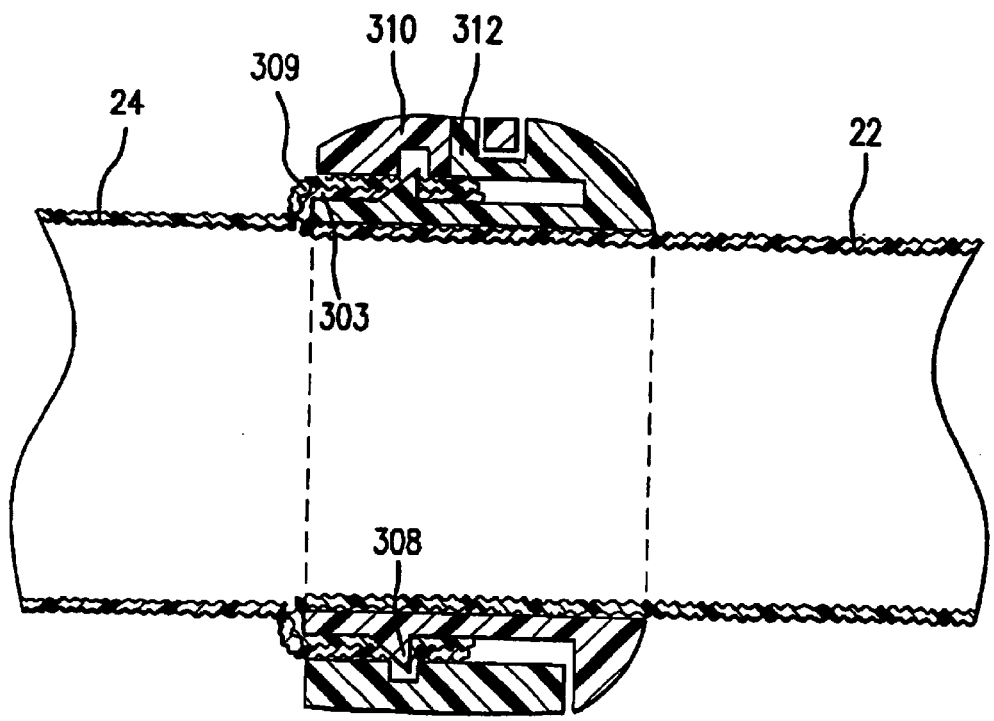
FIG. 16 is a cross-sectional representation of an assembled vascular prosthesis utilizing the connector body of FIG. 15.

In accordance with another embodiment of the invention, an alternative connector 20' is illustrated in cross-sectional representation in FIG. 15. A first prosthesis 22 extends through an interior bore 302 of connector body 300. An end portion 303 of the first prosthesis 22 is everted 304 and folded back over a first rim 306 of the connector body 300 and engaged along an exterior surface of the connector body, such as by detents 308. As illustrated in FIG. 16, a second prosthesis 24 intended to be joined to the first prosthesis 22 has an enlarged terminal portion 309 extended over the end portion 303 of the first prosthesis and engaged on detents 308. When properly positioned, strap 310 is circumscribed about the connector body 300 to firmly retain the connector in place. Throughout the assembly, handle 312 is used to manipulate the connector body.

Figure 17:
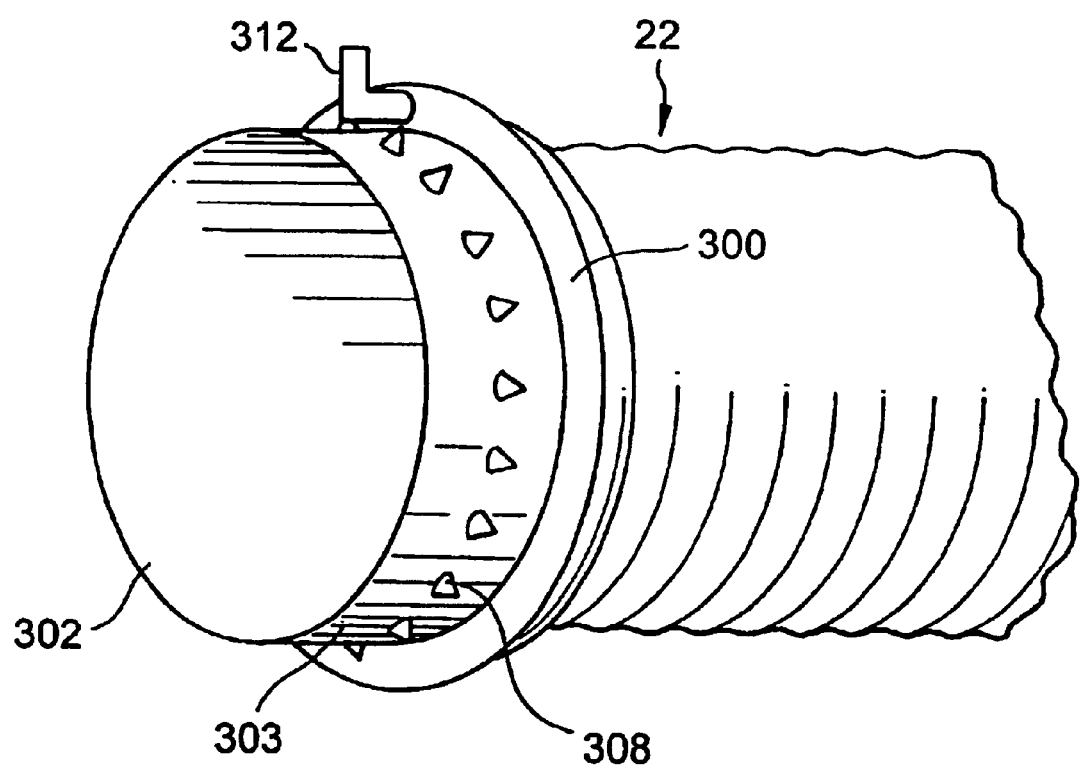
FIG. 17 is a perspective view of the connector body of FIG. 15.

The embodiment of FIG. 15 is further illustrated in perspective representation in FIG. 17 where first prosthesis 22 has been extended through the interior bore of connector body 300 and an end portion 303 everted and engaged on detents 308. Handle 312 provides ease of manipulation.

In the embodiment illustrated in FIGS. 15–17, the surface contacting the blood remains that of the prostheses, rather than a transition to the interior bore of the connector. Avoiding the changing of surface chemistry reduces the risk of thrombosis inherent when the chemistry of the surfaces contacted by the blood changes. Thrombogenicity is further reduced by a reduced turbulence imparted into the blood flow.

One or more embodiments of the present invention have been described. Nevertheless, it will be understood that various modifications may be made without departing from the spirit and scope of the invention. For example, the connectors may be tailored for a variety of general or specific applications. Accordingly, other embodiments are within the scope of the following claims.

What is claimed is:

1. A vascular connector for joining a first tubular vessel to a second tubular vessel, comprising:
    a connector body with a first connector body portion for engaging a first end of said first tubular vessel and a second connector body portion for engaging a first end of said second tubular vessel, said connector body extending for a length along a longitudinal axis;
    an extension projecting radially outward from said connector body and having opposing shaft portions extending substantially parallel to said longitudinal axis;
    a first locking strap for circumscribing said first connector body portion and said extension thereby preventing movement of said first tubular vessel relative to said connector body; and
    a second locking strap for circumscribing said second connector body portion thereby preventing movement of said second tubular vessel portion relative to said connector body.

2. The connector of claim 1 wherein a first radial array of detents extends outward from an exterior surface of said first connector body portion and a second radial array of detents extends outward from an exterior surface of said second connector body portion.

3. The connector of claim 2 wherein detents of said first radial array of detents outwardly terminate at an apex and said detents are effective to pierce and retain a wall of said first tubular vessel.

4. The connector of claim 2 wherein said extension has a length effective for grasping to facilitate manipulation of said connector body.

5. The connector of claim 4 wherein said extension is integral with said connector body.

6. The connector of claim 5 wherein said extension is unitary with said connector body.

7. The connector of claim 4 wherein said extension is removable from said first connector body portion.

8. The connector of claim 4 wherein said second tubular connector is a mirror image of said connector body.

9. The connector of claim 4 wherein said first locking strap is locked by engaging a first end thereof into a second end thereof.

10. The connector of claim 9 wherein said first locking strap is adapted so that locking is non-permanent and said first end thereof may be disengaged from said second end thereof.

11. The connector of claim 10 wherein said first end thereof includes a projection that engages a channel formed in a second end thereof.

12. The connector of claim 9 wherein said first tubular vessel and said second tubular vessel are both vascular prostheses.

13. The connector of claim 10 wherein said first locking strap is removable from said connector when unlocked.

* * * * *